(12) United States Patent
Nishiuchi et al.

(10) Patent No.: US 7,807,982 B2
(45) Date of Patent: Oct. 5, 2010

(54) PARTICLE BEAM IRRADIATION SYSTEM

(75) Inventors: Hideaki Nishiuchi, Hitachinaka (JP);
Kazuyoshi Saito, Hitachi (JP)

(73) Assignee: Hitachi, Ltd., Tokyo (JP)

( * ) Notice: Subject to any disclaimer, the term of this patent is extended or adjusted under 35 U.S.C. 154(b) by 359 days.

(21) Appl. No.: 11/692,331

(22) Filed: Mar. 28, 2007

(65) Prior Publication Data

US 2007/0228304 A1    Oct. 4, 2007

(30) Foreign Application Priority Data

Mar. 29, 2006    (JP) ............................. 2006-089840

(51) Int. Cl.
*H01J 49/00*    (2006.01)

(52) U.S. Cl. .............. 250/492.2; 250/492.1; 250/492.3; 250/493.1; 250/251; 607/1; 607/2

(58) Field of Classification Search ........................ None
See application file for complete search history.

(56) References Cited

U.S. PATENT DOCUMENTS

| | | | |
|---|---|---|---|
| 6,600,164 B1 * | 7/2003 | Badura et al. ............ | 250/492.3 |
| 6,614,038 B1 * | 9/2003 | Brand et al. ............. | 250/492.3 |
| 6,736,831 B1 * | 5/2004 | Hartmann et al. ............. | 607/1 |
| 6,745,072 B1 * | 6/2004 | Badura et al. .................. | 607/2 |
| 6,799,068 B1 * | 9/2004 | Hartmann et al. ............. | 607/2 |
| 7,053,389 B2 * | 5/2006 | Yanagisawa et al. ..... | 250/492.3 |
| 7,122,978 B2 * | 10/2006 | Nakanishi et al. ........... | 315/500 |
| 7,355,189 B2 * | 4/2008 | Yanagisawa et al. ..... | 250/503.1 |
| 7,385,203 B2 * | 6/2008 | Nakayama et al. .......... | 250/400 |
| 7,394,082 B2 * | 7/2008 | Fujimaki et al. ......... | 250/492.3 |
| 7,397,054 B2 * | 7/2008 | Natori et al. ............. | 250/492.3 |
| 7,456,415 B2 * | 11/2008 | Yanagisawa et al. ...... | 250/492.3 |
| 7,560,715 B2 * | 7/2009 | Pedroni .................... | 250/492.3 |

FOREIGN PATENT DOCUMENTS

| | | |
|---|---|---|
| JP | 5-198397 | 8/1993 |
| JP | 2596292 | 9/1997 |
| JP | 2004-529483 | 9/2004 |

OTHER PUBLICATIONS

Review of Scientific Instruments, Aug. 1993. vol. 64, No. 8, 2074-2093.
Proceedings of the Seventh Symposium on Accelerator and Related Technology for Application, Jun. 9-10, 2005, Tokyo, Japan, pp. 35-36.

* cited by examiner

*Primary Examiner*—David A Vanore
(74) *Attorney, Agent, or Firm*—Mattingly & Malur, P.C.

(57) ABSTRACT

It is an object of the present invention to provide a charged particle beam extraction method and particle beam irradiation system that make it possible to exercise intensity control over an extracted ion beam while a simple device configuration is employed. To accomplish the above object, there is provided a particle beam irradiation system comprising: a synchrotron for accelerating and extracting an charged particle beam; an irradiation apparatus for extracting the charged particle beam that is extracted from the synchrotron; first beam intensity modulation means for controlling the beam intensity of the charged particle beam extracted from the synchrotron during an extraction control period of an operation cycle of the synchrotron; and second beam intensity modulation means for controlling the beam intensity during each of a plurality of irradiation periods contained in the extraction control period of the operation cycle.

8 Claims, 13 Drawing Sheets

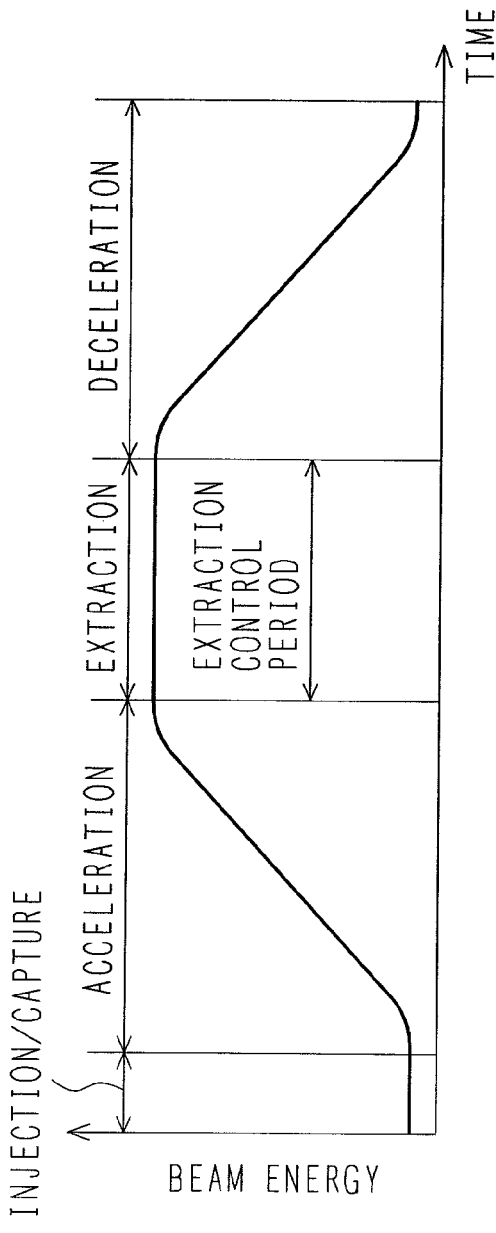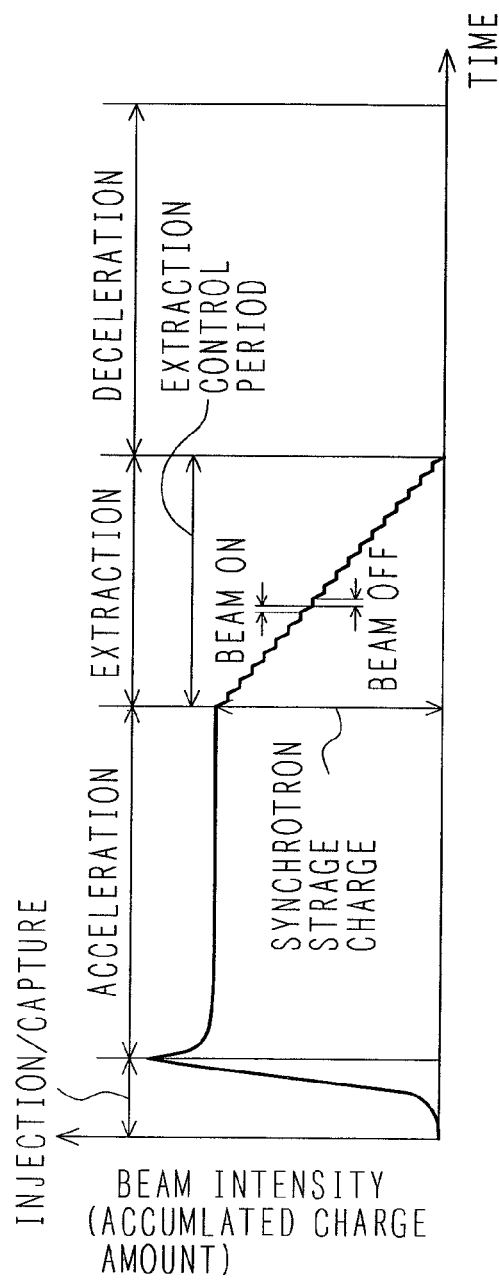

| ADDRESS | LOCAL MODULATION SIGNAL PATTERN DATA | BEAM EXTRACTION CONTROL PATTERN DATA |
|---|---|---|
| 0000 | 0 | 0 |
| 0001 | 0 | 0 |
| 0002 | 0 | 0 |
| 0003 | 1.000 | 1 |
| 0004 | 1.000 | 1 |
| 3996 | 1.000 | 1 |
| 3997 | 0 | 0 |
| 3998 | 0 | 0 |
| 3992 | 0 | 0 |

DATA UPDATE PROCESSING SIGNAL

PARTICLE BEAM IRRADIATION SYSTEM

BACKGROUND OF THE INVENTION

1. Field of the Invention

The present invention relates to a particle beam irradiation system, and more particularly to a particle beam irradiation system that is suitably applicable to a particle beam therapy system, which provides cancer treatment by irradiating a diseased part with a proton, heavy ion, or other charged particle beam.

2. Description of the Related Art

Particle beam therapy is known as radiological therapy of cancer. In particle beam therapy, a patient's cancerous part is irradiated with a proton, heavy ion, or other ion beam for therapy purposes. A particle beam therapy system that provides particle beam therapy includes an ion beam generator, a beam transport line, and an irradiation apparatus. The ion beam generator includes a synchrotron or cyclotron that accelerates an ion beam, which moves in a circular path, to a desired energy.

The synchrotron includes a radiofrequency acceleration system (radiofrequency acceleration cavity), an extraction radiofrequency electrode, and an extraction deflector (refer, for instance, to Patent Document 1). The radiofrequency acceleration system applies a radiofrequency voltage to the ion beam, which moves in a circular path, to accelerate the ion beam to a target energy. The extraction radiofrequency electrode increases the betatron oscillation amplitude of the ion beam, which moves in a circular path. The extraction deflector removes the ion beam from its circular path. When the ion beam accelerated to the target energy is to be extracted from the synchrotron to the beam transport line, the extraction radiofrequency electrode applies a radiofrequency magnetic field or radiofrequency electric field (hereinafter referred to as the radiofrequency signal) to the ion beam to increase the betatron oscillation amplitude, which represents the intrinsic oscillation of the ion beam that moves in a circular path. After the betatron oscillation amplitude is increased, the ion beam moves beyond a stability limit, is extracted from the synchrotron to the beam transport line, and is transported to the irradiation apparatus.

The cyclotron receives the ion beam, which is supplied from an ion source, applies a radiofrequency voltage to the ion beam in a uniform magnetic field within the cyclotron, and causes the ion beam to move out of the circular path. After being accelerated to the target energy, the ion beam is extracted to the beam transport line and transported to the irradiation apparatus.

The irradiation apparatus shapes the ion beam, which is introduced from the ion beam generator, in accordance with the depth from the patient body surface and the shape of a diseased part, and irradiates the diseased part of a patient in a therapy bed with the shaped ion beam. The irradiation apparatus irradiates the diseased part with the ion beam by using an appropriate beam irradiation method. In general, the irradiation apparatus uses a double scatterer method (Non-patent Document 1, page 2081, FIG. 35, wobbler method (Non-patent Document 1, page 2084, FIG. 41), or beam scanning method (Patent Document 1 or Non-patent Document 1, pages 2092 and 2093).

The diseased part usually has a certain thickness in the direction of ion beam propagation in a patient body. To irradiate the whole thickness of the diseased part with the ion beam, it is necessary to control the energy of the ion beam so as to form a uniform absorbed dose range (spread-out Bragg peak or SOBP) having a certain width in the direction of ion beam propagation. An irradiation method that uses a range modulation wheel (hereinafter referred to as the RMW) is proposed as energy control means for forming a desired SOBP. The RMW is a rotating structure and has a plurality of wedge-shaped energy absorbers arranged in circumferential direction so that the thickness of a region through which the ion beam passes varies with time. When the RMW rotates, the thickness in the direction of ion beam propagation (the axial direction of the RMW) increases or decreases. An RMW-based irradiation method (Non-patent Document 1, page 2077, FIG. 30) is called an RMW irradiation method.

The irradiation apparatus shapes the ion beam in accordance with the depth from the patient body surface and the shape of a diseased part. However, the intensity of the beam incident on the diseased part is adjusted by the ion beam generator. In the synchrotron, the beam intensity of the ion beam that is extracted from the ion beam generator is controlled as desired by adjusting the intensity of the radiofrequency signal to be applied to the extraction radiofrequency electrode. The cyclotron includes a device that adjusts the intensity of an extracted ion beam (refer, for instance, to Patent Document 2). More specifically, the cyclotron measures the intensity of an actually extracted beam, and exercises control in accordance with the measurement result to regulate an arc current that is to be supplied to the ion source.

Patent Document 1: Japanese Patent No. 2596292
Patent Document 2: JP-A-2004-529483 (PCT)
Non-patent Document 1: Review of Scientific Instruments, Volume 64, Number 8 (August 1993), pages 2074-2093
Non-patent Document 2: Proceedings of the Symposium on Accelerator and Related Technology for Application, Volume 7 (June 2005), pages 35-36

SUMMARY OF THE INVENTION

The synchrotron receives the ion beam, which is extracted from a preaccelerator, accelerates the received ion beam to a desired energy, and extracts the accelerated ion beam. The synchrotron repeatedly performs an operation cycle that includes receiving an incoming ion beam, accelerating the received ion beam, and extracting the accelerated ion beam. Therefore, the ion beam is supplied to the synchrotron only at the time of receiving the incoming ion beam within an operation cycle unlike the ion beam supply to the cyclotron. The accumulated amount of ion beam accelerated by the synchrotron is maximized at the end of acceleration and decreases as the extraction control time elapses (Non-patent Document 1). Further, it is known that the relationship between the amplitude of the radiofrequency signal to be applied to the extraction radiofrequency electrode and the intensity of the beam extracted from the synchrotron is also affected by the accumulated amount of ion beam within the synchrotron. Therefore, it is not easy to extract an ion beam having a desired intensity.

A method proposed, for instance, by Non-patent Document 2 provides outgoing beam intensity control by making an extraction process model in consideration of ion beam diffusion by the extraction radiofrequency signal to be applied to the ion beam, estimating the intensity of the ion beam, which moves circularly within the synchrotron, from the number of particles extracted by a requested beam intensity signal, optimizing the amplitude modulation pattern of the radiofrequency signal accordingly, and determining the address of an associated intensity pattern. However, if Non-patent Document 2 is applied, it is necessary to provide means of estimating the intensity of a beam moving circularly within the synchrotron, which varies with extraction control. This complicates the adjustment for causing the estimation result to match the intensity control result of an actually extracted ion beam. Consequently, the resulting control device configuration is complicated.

It is an object of the present invention to provide a charged particle beam extraction method and particle beam irradiation system that make it possible to exercise intensity control over an extracted ion beam while a simple device configuration is employed.

To accomplish the above object, there is provided a particle beam irradiation system comprising: a synchrotron for accelerating and extracting an ion beam; an irradiation apparatus for radiating the ion beam extracted from the synchrotron; first beam intensity modulation means for controlling the beam intensity of the ion beam extracted from the synchrotron during an extraction control period of an operation cycle of the synchrotron; and second beam intensity modulation means for controlling the beam intensity during each of a plurality of irradiation periods contained in the extraction control period of the operation cycle.

It is preferred that the irradiation apparatus include a rotatable energy moderator whose axial direction thickness varies with the direction of rotation, and extract the ion beam that is transmitted through the energy moderator, and that the second beam intensity modulation means control the beam intensity in accordance with the rotation angle of the energy moderator.

The present invention makes it possible not only to accurately control the outgoing beam intensity in accordance with the accumulated amount of ion beam that moves circularly within the synchrotron, but also to accurately control the intensity of an ion beam that falls on a radiation target.

BRIEF DESCRIPTION OF THE DRAWINGS

FIGS. 2A and 2B illustrate the operation of a synchrotron, in which FIG. 2A shows how beam energy changes during one cycle of the synchrotron and FIG. 2B shows how beam intensity changes during one cycle of the synchrotron;

DETAILED DESCRIPTION OF THE PREFERRED EMBODIMENTS

Embodiments of the present invention will be described below.

First Embodiment

Figure 1:
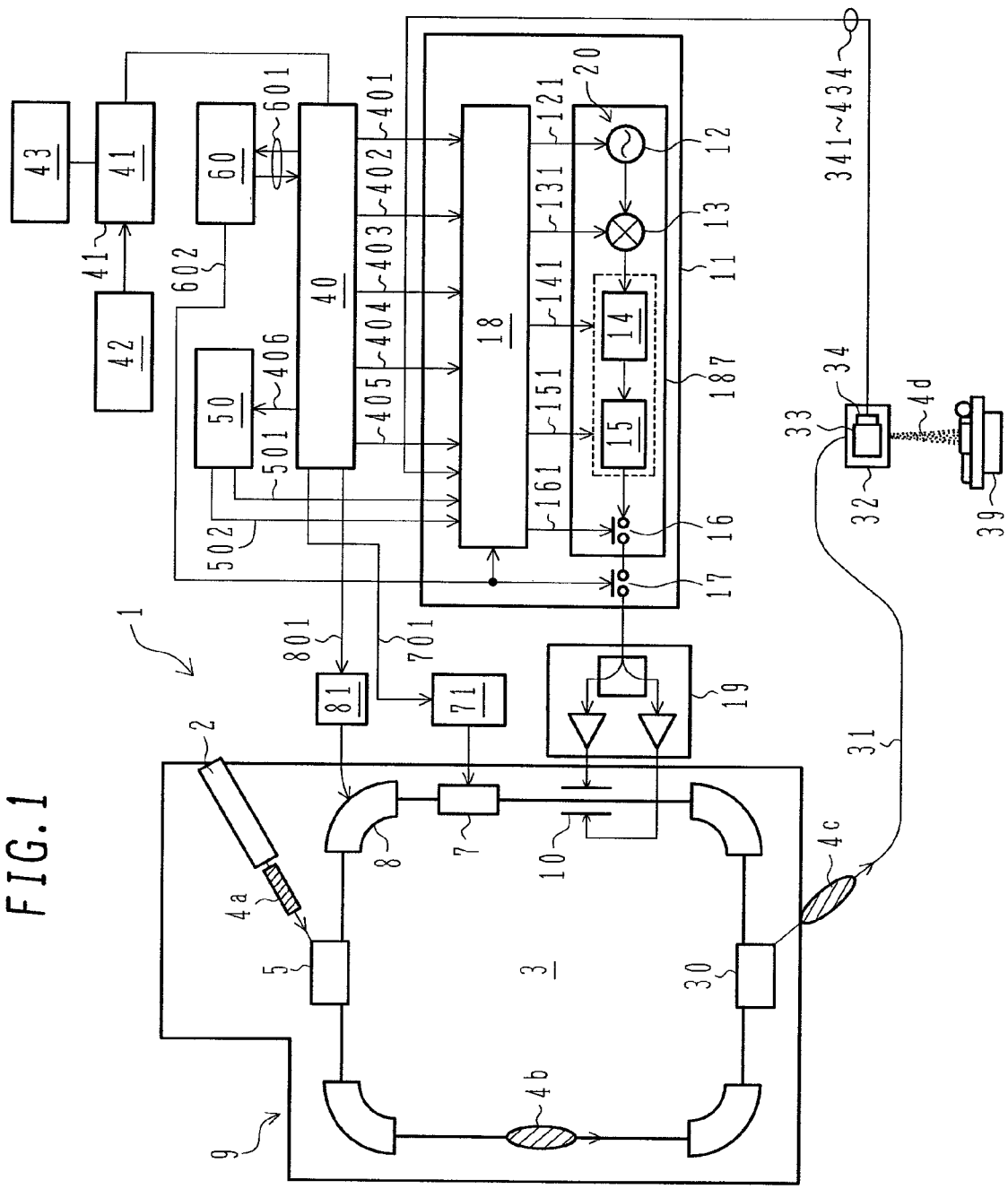
FIG. 1 shows the configuration of a particle beam therapy system according to a first embodiment of the present invention.

A particle beam therapy system according to a first embodiment of the present invention will now be described with reference to FIGS. 1 and 7. As shown in FIG. 1, the particle beam therapy system 1 according to the present embodiment includes an ion beam generator 9, a beam transport apparatus 31, and an irradiation field formation apparatus (charged particle beam irradiation apparatus; hereinafter referred to as the irradiation apparatus) 32. The beam transport apparatus 31 provides communication between the ion beam generator 9 and the irradiation apparatus 32, which is installed in a therapy room.

The ion beam generator 9 includes an ion source (not shown), a preaccelerator 2, and a synchrotron 3. The ion source is connected to the preaccelerator 2. The synchrotron 3 is configured so that an injector 5, a radiofrequency accelerator (acceleration cavity) 7, a plurality of bending magnets 8, a plurality of quadrupole magnets (not shown), a radiofrequency electrode (radiofrequency application apparatus) for extraction 10, and an extraction apparatus 30 are positioned in a circular path. The preaccelerator 2 is connected to the injector 5. The acceleration cavity 7 is connected to a radiofrequency power supply (not shown) that applies radiofrequency power. The radiofrequency power supply is controlled by a radiofrequency acceleration control apparatus 71. The bending magnets 8 are connected to a bending magnet power supply 81. The radiofrequency electrode 10 is connected to an extraction control apparatus 11 via an extraction power amplifier 19.

The extraction control apparatus 11 includes an extraction radiofrequency signal processor (radiofrequency signal generator) 20, a radiofrequency switch 17, and an extraction control signal processor 18. The extraction radiofrequency signal processor 20 includes a radiofrequency oscillator 12, a radiofrequency mixer 13, amplitude control means 187, and a radiofrequency switch 16. The amplitude control means 187 includes a first intensity modulator (hereinafter referred to as the global intensity modulator) 14 and a second intensity modulator (hereinafter referred to as the local intensity modulator) 15. The radiofrequency oscillator 12 outputs a radiofrequency signal, which is transmitted to the extraction power amplifier 19 through the radiofrequency mixer 13, global intensity modulator 14, local intensity modulator 15, and two radiofrequency switches 16, 17.

Figure 7:
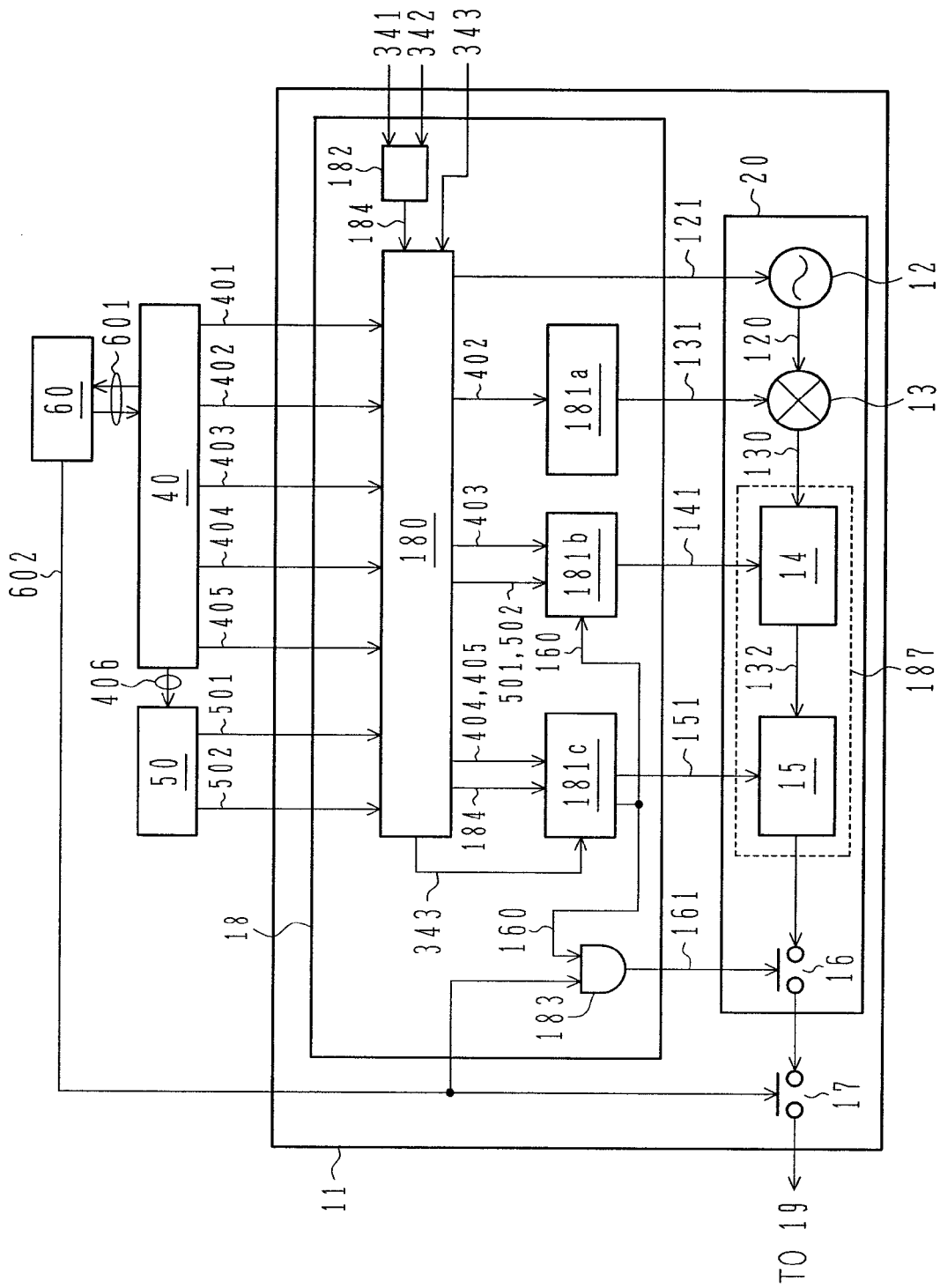
FIG. 7 shows the configuration of an extraction control apparatus that is operated according to the RMW irradiation method.

As shown in FIG. 7, the extraction control signal processor 18 includes a control processor for extraction 180, control signal output units 181*a*, 181*b*, 181*c*, a multiplier circuit 182, and an AND circuit 183. The multiplier circuit 182 is connected to the control processor 180. The control processor 180 is connected to the radiofrequency oscillator 12 and control signal output units 181*a*, 181*b*, 181*c*. The control signal output unit 181*a* is connected to the radiofrequency mixer 13. The control signal output unit 181*b* is connected to the global intensity modulator 14. The control signal output unit 181c is connected to the local intensity modulator 15, control signal output unit 181b, and AND circuit 183. The AND circuit 183 is connected to the radiofrequency switch 16.

As shown in FIG. 1, a therapy plan unit 43 is connected to an integrated control apparatus 41, which includes a storage device 42. The integrated control apparatus 41 is connected to an accelerator system control apparatus 40. The accelerator system control apparatus 40 is connected to the radiofrequency acceleration control apparatus 71, the bending magnet power supply 81, a timing system 50, a safety interlock system 60, and the extraction control apparatus 11. The timing system 50 is connected to the extraction control apparatus 11. The safety interlock system 60 is connected to the radiofrequency switch 17 and AND circuit 183.

The beam transport apparatus 31 is connected to the synchrotron 3 and irradiation apparatus 32. The irradiation apparatus 32 includes an RMW (beam energy modulator) 33, a rotation detector (a rotary encoder in the present embodiment) 34 for detecting the rotation angle of the RMW 33, and a dose monitor (not shown). The rotary encoder 34 is connected so as to detect the rotation of the RMW 33. The output signal from the rotary encoder 34 is transmitted to the multiplier circuit 182 and control processor 180, which are included in the extraction control signal processor 18.

Figures 3A, 3B:
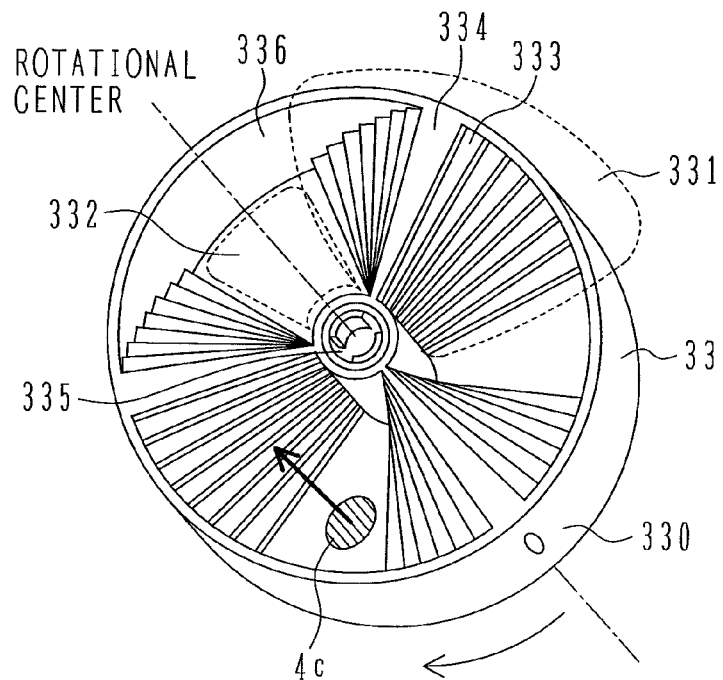
FIG. 3A is a perspective view illustrating an RMW and FIG. 3B shows a memory map.

FIG. 3A shows the structure of the RMW 33. The RMW 33 includes a rotation shaft 335; a cylindrical member 336, which is concentric with the rotation shaft 335; and a plurality of vanes (three vanes in the present embodiment) 331 that are extended in the direction of the radius of the RMW 33, which is installed over the rotation shaft 335. These vanes 331 are formed so that the width in circumferential direction increases as they are extended outward in radial direction. Each vane 331 has a plurality of planar areas 333 that are positioned stepwise in the circumferential direction of the RMW 33. The thicknesses between the planar areas 333 and the bottom surface of the RMW 33 in the axial direction of the RMW differ from each other. The thickness relative to a planar area 333 is referred to as the planar area thickness. A thin vane base 332 is formed between the vanes 331 in the circumferential direction of the RMW 33. In the RMW 33 according to the present embodiment, three vane bases (or openings) 332 exist. These vane bases 332 are formed between the three vanes 331. The vanes 331 are formed so that the thickness of each planar area increases from the vane bases 332 on both ends of the vanes 331 in circumferential direction toward a planar area 333, which is positioned on a vane top 334 that is thick in the direction of beam propagation. The cylindrical member 336 is provided with an origin point sensor 330, which is used to observe the rotation period of the RMW 33.

The signal output from the rotary encoder 34 will now be described with reference to FIGS. 6 and 7. The rotary encoder 34 detects the rotation angle (rotation phase) of the rotation shaft 335 (RMW 33), which is rotating, and outputs a layer A signal 341 and a layer B signal 342 to the multiplier circuit 182 in accordance with the detected rotation angle (FIG. 7). The layer A signal 341 (FIG. 6-(*a*)) and layer B signal 342 (FIG. 6-(*b*)) are pulse signals that carry the rotation angle information about the RMW 33. The phase difference between the layer A signal 341 and layer B signal 342 is 90 degrees. The rotary encoder 34 according to the present embodiment outputs 1000 pulses of layer A signal 341 and layer B signal 342, respectively, per rotation of the RMW 33. While the RMW 33 is rotating, the rotary encoder 34 constantly outputs the layer A signal 341 and layer B signal 342 at a frequency according to the rotation speed. Upon receipt of the layer A signal 341 and layer B signal 342, the multiplier circuit 182 samples the rising and falling edges of the layer A signal 341 and layer B signal 342, multiplies the signals by four, and outputs the resulting signals (hereinafter referred to as the update clock signals) 184 (FIG. 6-(*d*)). Therefore, the multiplier circuit 182 generates 4000 pulses of update clock signals 184 per rotation of the RMW 33 and outputs them to the control processor 180. The control processor 180 outputs the update clock signals 184 to the control signal output unit 181c.

Figure 6:
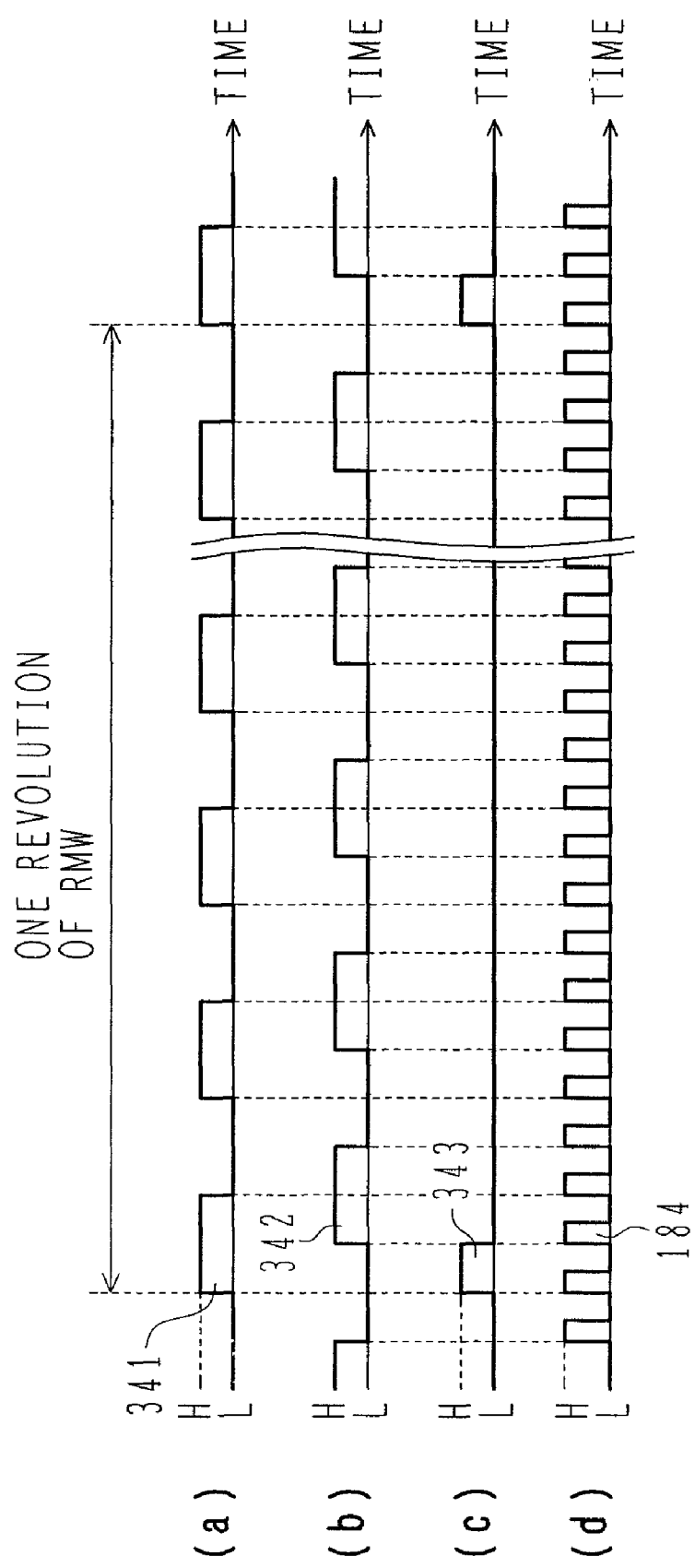
FIG. 6 is a timing diagram illustrating one revolution of the RMW that is operated according to the RMW irradiation method.

Further, the rotary encoder 34 outputs an origin point signal 343 once during each rotation of the RMW 33 (FIG. 6-(*c*)). While the RMW 33 is rotating, the origin point signal 343 is constantly output at a frequency according to the rotation speed. The control processor 180 outputs the origin point signal 343 to the control signal output unit 181c.

A doctor inputs patient information (diseased part location and size, beam irradiation direction, and maximum irradiation depth) into the therapy plan unit 43. The therapy plan unit 43 uses therapy plan software to calculate the SOBP width, the irradiation field size, the target dose for a diseased part, and other data necessary for therapy in accordance with the input patient information. Further, the therapy plan unit 43 uses the therapy plan software to calculate the energy of beam extraction from the synchrotron (extraction energy) 3, the location of a therapy bed 39, the RMW rotation angles for starting and stopping a beam extraction operation, and various other operation parameters, and select an appropriate RMW 33 for therapy. These pieces of therapy plan information (SOBP width, irradiation field size, target dose, various operation parameters, extraction energy, information about the selected RMW 33, etc.) are input into the integrated control apparatus 41 and stored in the storage device 42 in the integrated control apparatus 41.

The therapy plan information is displayed on a display device (not shown) that is positioned in a control room within the therapy room in which preparations for therapy are made. A radiological technician observes a screen of the display device to note the selected RMW 33, and sets the selected RMW 33 in the irradiation apparatus 32.

In accordance with instructions from the integrated control apparatus 41, a therapy bed control apparatus (not shown) moves the therapy bed 39 to which a patient is fastened, and positions the patient's diseased part (irradiation target) on an extended line of a beam axis. The accelerator control system 40 determines the irradiation beam energy from the therapy plan information fed from the integrated control apparatus 41, transmits a control command (electrical current setting information) 801 to the bending magnet power supply 81, and transmits a control command (frequency setting information) 701 to the radiofrequency acceleration control apparatus 71. The bending magnet power supply 81 excites the bending magnets 8 in accordance with the control command 801. In accordance with the control command 701, the radiofrequency acceleration control apparatus 71 activates a radiofrequency power supply that is connected to the radiofrequency accelerator 7. The radiofrequency power supply applies a radiofrequency to the acceleration cavity 7. The integrated control apparatus 41 outputs an RMW rotation control signal to drive a motor while making preparations for ion beam acceleration. This causes the RMW 33 to rotate in the direction of an arrow in FIG. 3A. The rotary encoder 34 outputs a rotation detection signal in accordance with the rotation of the RMW 33.

The doctor manipulates an operation panel in the aforementioned control room to output an irradiation start signal to the integrated control apparatus 41. In accordance with the irradiation start signal, the preaccelerator 2 accelerates an ion beam (e.g., a beam of protons (or carbon ions or other heavy particles) that is generated from the ion source, and supplies the accelerated ion beam to the synchrotron 3.

The synchrotron 3 further accelerates the ion beam 4a, which is injected from the preaccelerator. In this beam acceleration control process, the radiofrequency voltage supplied from the radiofrequency power supply is developed in a gap within the acceleration cavity 7, and the ion beam 4b that moves circularly within the synchrotron 3 is allowed to pass through the cavity gap. Thus, energy is given to the ion beam for acceleration purposes. In this instance, the bending magnetic field strength increases with an increase in energy and the frequency of the radiofrequency voltage applied to the acceleration cavity increases. Thus, the ion beam 4b can be accelerated while it steadily moves in a circular path within the synchrotron 3. After the ion beam 4b is accelerated to a target beam energy, the radiofrequency electrode 10 applies a radiofrequency so that the ion beam 4b is extracted from the synchrotron 3.

The ion beam 4c, which is extracted from the synchrotron 3, travels though the extraction apparatus 30 and beam transport apparatus 31, and reaches the irradiation apparatus 32. Further, the ion beam travels along a beam path, which extends in the axial direction of the irradiation apparatus 32 (in the direction of ion beam propagation), in the irradiation apparatus 32, passes through the rotating RMW 33, and falls on the patient's diseased part. The dose monitor (now shown) measures the dose of ion beam incident on the diseased part. When the amount of radiation administered to the diseased part reaches a target dose, the measurement result generated by the dose monitor is conveyed to the integrated control apparatus 41. The integrated control apparatus 41 then stops the ion beam extraction from the synchrotron 3. This terminates the ion beam radiation to the patient.

Figure 4:
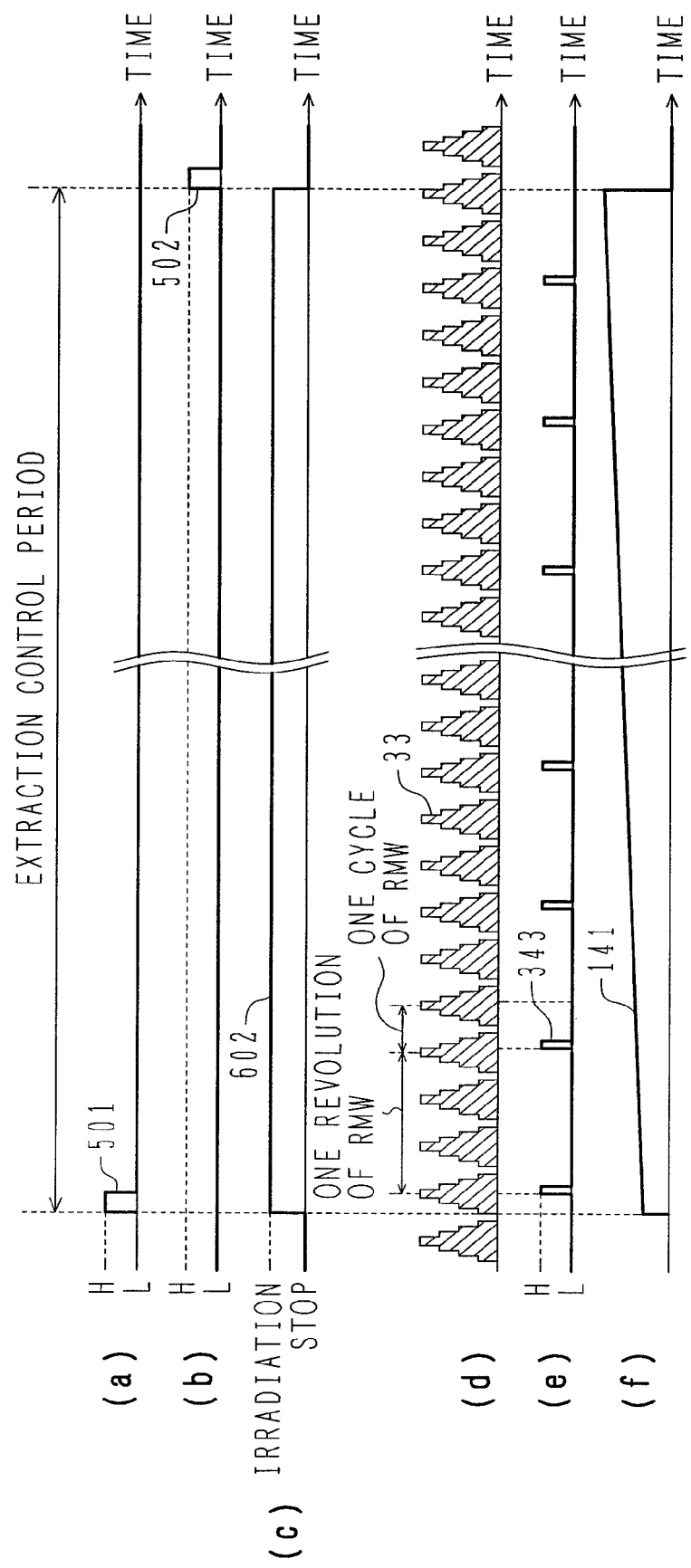
FIG. 4 is a timing diagram illustrating a radiation control period of an operation cycle of the synchrotron that is operated according to an RMW irradiation method.

As shown in FIG. 2A, the synchrotron 3 operates by repeating an ion beam injection/capture process, a process for accelerating the ion beam to a preselected energy, a process for extracting the ion beam that is accelerated to a target energy, and a deceleration process. The injection/capture, acceleration, extraction, and deceleration processes (which constitute an operation cycle of the synchrotron 3) are controlled in accordance with the energy of the ion beam to be accelerated. When the ion beam moving in a circular path within the synchrotron 3 is accelerated to a target energy, the timing system 50 outputs an extraction control start signal 501. Further, when the ion beam extraction process is to be stopped within an operation cycle of the synchrotron 3, the timing system 50 outputs an extraction control termination signal 502. The time interval between the instant at which the timing system 50 outputs the extraction control start signal 501 (a point of rising to the H level in FIG. 4-(a)) and the instant at which the timing system 50 outputs the extraction control termination signal 502 (a point of rising to the H level in the figure) is called an extraction control period. The synchrotron 3 can supply the ion beam to the irradiation apparatus 32 during the extraction control period.

The beam intensity of the ion beam moving in a circular path within the synchrotron 3 (the accumulated charge amount of the circular beam) changes in accordance with the operation of the synchrotron 3 (FIG. 2A), as shown in FIG. 2B. When the ion beam is injected into the synchrotron 3 and captured, the beam intensity gradually increases. The beam intensity attenuates at an early stage of acceleration control because an ion beam loss is caused, for instance, by a space charge effect. However, the beam intensity substantially remains unchanged between the middle and end of an acceleration period. In the synchrotron, the beam intensity prevailing at the end of acceleration is equivalent to the accumulated charge amount. Therefore, when the ion beam is extracted from the synchrotron 3, the intensity of the circular beam gradually attenuates. In the present embodiment, the beam intensity varies stepwise because the extraction of an ion beam repeatedly starts (beam on) and stops (beam off). The intensity of a circular ion beam attenuates when the ion beam is supplied out of the synchrotron 3 due to ion beam extraction control, and does not attenuate when the ion beam is not supplied out of the synchrotron 3 while ion beam extraction control is halted. An ion beam that is not extracted during an extraction control period and remains in the synchrotron 3 is decelerated to a low energy and annihilated due to subsequent deceleration control.

In the present embodiment, an ion beam is extracted from the synchrotron 3 when the extraction radiofrequency signal processor 20 applies an extraction radiofrequency signal 133 to the radiofrequency electrode 10. The functions of the extraction radiofrequency signal processor 20, which includes the above signal application mechanism, will now be described with reference to FIGS. 1 and 7.

First of all, the accelerator control system 40 outputs the information about the frequency to be set in the radiofrequency oscillator 12 (oscillator control data) 401 to the extraction control signal processor 18 as shown in FIG. 7. This frequency is determined in accordance with the energy of the beam extracted from the synchrotron 3. The extraction control signal processor 18 outputs a frequency when the control processor 180 acquires the oscillator control data 401 and sets a radiofrequency signal output command 121 in the radiofrequency oscillator 12 in accordance with the oscillator control data 401. Similarly, the accelerator control system 40 outputs band limit radiofrequency signal pattern data 402 to the extraction control signal processor 18. As is the case with the oscillator control data 401, the band limit radiofrequency signal pattern data 402 is determined in accordance with the energy of the beam extracted from the synchrotron 3. The extraction control signal processor 18 causes the control processor 180 to acquire the band limit radiofrequency signal pattern data 402 and stores the input band limit radiofrequency signal pattern data 402 in the storage device (not shown) that is included in the control signal output unit 181a. The accelerator control system 40 outputs global intensity modulation signal pattern data 403 to the extraction control signal processor 18. The global intensity modulation signal pattern data 403 is determined in consideration of the fact that the beam intensity prevailing within the synchrotron 3 varies with time when an ion beam is extracted from the synchrotron 3. More specifically, the global intensity modulation signal pattern data 403 is derived from the relationship between the beam intensity of the ion beam remaining in the synchrotron 3 and the intensity of the extraction radiofrequency signal to be applied to the extraction radiofrequency electrode 10. The extraction control signal processor 18 causes the control processor 180 to acquire the global intensity modulation signal pattern data 403 and stores it in the storage device (not shown) that is included in the control signal output unit 181b. The accelerator control system 40 outputs local modulation signal pattern data 404 and beam extraction control pattern data 405 to the extraction control signal processor 18. The local modulation signal pattern data 404 and beam extraction control pattern data 405 are determined in accordance with the therapy plan information. The extraction control signal processor 18 causes the control processor 180 to acquire the local modulation signal pattern data 404 and beam extraction control pattern data 405 and stores them in the storage device (not shown) that is included in the control signal output unit 181c. The storage device stores the local modulation signal pattern data 404 and beam extraction control pattern data 405 by using a memory map that looks like FIG. 3B. In the present embodiment, which is shown in FIG. 3B, addresses and data are expressed in decimal notation. In the memory map shown in FIG. 3B, the addresses correspond to the update clock signal 184, which is output in accordance with the rotation of the RMW 33. The memory map is structured so that the memory address is updated from the lowest-order address to the highest-order address when the RMW 33 makes one revolution. The value "1" in the beam extraction control pattern data 405 permits the ion beam to be extracted. The value "0" in the beam extraction control pattern data 405 stops the ion beam from being extracted. The local modulation signal pattern data 404 is expressed within a range from "0" to "1." The value "0" represents the lowest intensity of the ion beam to be extracted, that is, indicates that the ion beam extraction should be stopped. The value "1" represents the highest intensity of the ion beam to be extracted.

Before an ion beam is extracted from the synchrotron 3, the accelerator control system 40 confirms, for instance, the operating status and operation control status of each component of the particle beam therapy system 1. When the components are normal, the accelerator control system 40 outputs a normality signal 601 to the safety interlock system 60 as shown in FIG. 7. The normality signal indicates that each component is normal. Upon receipt of the normality signal 601, the safety interlock system 60 starts transmitting a beam extraction permission signal 602 to the radiofrequency switch 17 and AND circuit 183. The radiofrequency switch 17 remains closed while the beam extraction permission signal 602 is being input.

The radiofrequency oscillator 12 outputs a radiofrequency reference signal 120 having a preselected frequency to the radiofrequency mixer 13.

The control signal output unit 181a generates a band limit radiofrequency signal 131 in accordance with the stored band limit radiofrequency signal pattern data 402, and outputs the band limit radiofrequency signal 131 to the radiofrequency mixer 13. The radiofrequency mixer 13 mixes (combines) the radiofrequency reference signal 120 and band limit radiofrequency signal 131, and generates a band radiofrequency signal 130, which is obtained by superposing the band limit radiofrequency signal 131 over both sidebands relative to a center frequency that is represented by the radiofrequency reference signal 120. The radiofrequency mixer 13 outputs the band radiofrequency signal 130 to the global intensity modulator 14.

In accordance with the global intensity modulation signal pattern data 403 stored in the storage device, the control signal output unit 181b generates a global intensity modulation signal 141 and outputs it to the global intensity modulator 14. The global intensity modulation signal 141 provides control so that the extracted beam intensity does not vary with time when an ion beam is extracted from the synchrotron 3. The global intensity modulator 14 outputs a radiofrequency signal 132 that is obtained by modulating the band radiofrequency signal 130 in accordance with the global intensity modulation signal 141. The radiofrequency signal 132, which is output from the global intensity modulator 14, is output to the local intensity modulator 15.

In accordance with the local modulation signal pattern data 404 stored in the storage device, the control signal output unit 181c generates a local modulation signal 151 and outputs it to the local intensity modulator 15. The local modulation signal 151 controls the intensity of the ion beam to be radiated in accordance with the rotation angle of the RMW 33. The local intensity modulator 15 modulates the radiofrequency signal 132 in accordance with the local modulation signal 151 and generates the extraction radiofrequency signal 133. The extraction radiofrequency signal 133 is output to the power amplifier 19 via the radiofrequency switches 16, 17, which are closed by the beam extraction permission signal 602. The power amplifier 19 amplifies the extraction radiofrequency signal 133 and applies it to the radiofrequency electrode 10. The ion beam moving in a circular path within a stability limit is shifted out of the stability limit and extracted from the synchrotron 3 when the extraction radiofrequency signal 133 is applied to the radiofrequency electrode 10.

If any fault occurs in a component of the particle beam therapy system 1 to obstruct the beam radiation to the patient during irradiation control, the accelerator control system 40 outputs an abnormality signal 601 to the safety interlock system 60, thereby indicating that a component is abnormal. The safety interlock system 60 receives the abnormality signal 601 as a stop command for the beam extraction permission signal 602, and immediately stops the output of the beam extraction permission signal 602. The radiofrequency switch 17 opens when the output of the beam extraction permission signal 602 stops. When the radiofrequency switch 17 opens, the application of the extraction radiofrequency signal 133 to the radiofrequency electrode 10 stops. In this manner, the synchrotron 3 provides interlock control to stop the ion beam extraction.

The uniform SOBP width that is formed within the body of the patient is adjusted by changing the RMW rotation angle prevailing at the beginning of ion beam extraction and the RMW rotation angle prevailing at the end of ion beam extraction. The function that is exercised in accordance with the present embodiment to adjust the SOBP width by opening/closing the radiofrequency switch 16 in accordance with the rotation angle of the RMW 33 will be described below.

First of all, open/close control over the radiofrequency switch 16 will be described. As shown in FIG. 7, the origin point signal 343 from the rotary encoder 34, which detects the rotation angle of the RMW 33, is input to the extraction control signal processor 18 and transmitted to the control processor 180. The control processor 180 outputs the origin point signal 343 to the control signal output unit 181c. Upon receipt of the origin point signal 343, the control signal output unit 181c accesses the storage device (not shown) for the control processor 180 having the information shown in FIG. 3B, and reads the beam extraction control pattern data 405 that is positioned at an initial address (the present embodiment assumes that a start address, which is "0000," is the initial address). If the read beam extraction control pattern data 405 is "0," the control signal output unit 181c outputs a beam extraction control signal (OFF signal) 160 that terminates the ion beam radiation. If, on the other hand, the read beam extraction control pattern data 405 is "1," the control signal output unit 181c outputs a beam extraction control signal (ON signal) 160 that permits the ion beam radiation. When the control processor 180 transmits a pattern data update signal 184, the control signal output unit 181c accesses the storage device and reads the beam extraction control pattern data 405 that is positioned at the next address, which is "0001." If the read beam extraction control pattern data 405 is "0," the control signal output unit 181c outputs a beam extraction control signal 160 that is an OFF signal. If, on the other hand, the read beam extraction control pattern data 405 is "1," the control signal output unit 181c outputs a beam extraction control signal 160 that is an ON signal. A series of processing steps for updating the address of data stored in the storage device in accordance with an input pattern data update signal 184, reading the data stored at the updated address, outputting a control signal in accordance with the data, and waiting for an input of the next pattern data update signal 184 is called a data update. The control signal output unit 181c repeatedly performs the above data update. When the address is an end address, which is "3999," the control signal output unit 181c automatically performs an address update to access the start address, which is "0000," and reads the beam extraction control pattern data 405 that is stored at the start address. The information stored in the storage device has a ring-shaped memory access structure as described above. The use of such a ring-shaped memory access structure makes it possible to provide output control in synchronism with RMW rotation. When the signal output from the origin point sensor 330 for the RMW 33 and an origin point signal (Z-phase signal) 343 that is output from the rotation detector 34 differ in phase or when a phase difference arises between RMW beam passage phase and control output data, such a physical device phase difference can be corrected with the output initial address of the pattern data by arbitrarily changing the initial address of the pattern memory. An external origin point detection circuit may be additionally provided for the RMW 33, and a signal output from this circuit may be used as an origin point signal instead of the origin point signal 343 that is output from the rotary encoder 34. In the present embodiment, the beam extraction control pattern data 405 at address "0000" is "0" as shown in FIG. 3B. Therefore, the control signal output unit 181c to which the origin point signal 343 is input outputs a beam extraction control signal that is an OFF signal. The control signal output unit 181c outputs a beam extraction control signal 160, which looks like FIG. 5-(d), by inputting the pattern data update signal 184 from the control processor 180, repeatedly performing a data update, and outputting the read beam extraction control signal 160. In other words, in a region (irradiation period Tb) where the vanes 331 are relatively thin at and near the vane bases 332 in the circumferential direction of the RMW 33, the control signal output unit 181c outputs a beam extraction control signal 160 that is an ON signal for permitting the ion beam radiation. In the other rotation angle region, the control signal output unit 181c outputs a beam extraction control signal 160 that is an OFF signal for terminating the ion beam radiation.

If a beam extraction control signal 160 that is an ON signal for permitting the ion beam radiation is input while the beam extraction permission signal 602 is input from the safety interlock system 60, the AND circuit 183 closes the radiofrequency switch 16 upon receipt of a command signal 161. If, on the other hand, a beam extraction control signal 160 that is an OFF signal for terminating the ion beam radiation is input while the beam extraction permission signal 602 is input from the safety interlock system 60, the AND circuit 183 opens the radiofrequency switch 16 upon receipt of the command signal 161.

Since the present embodiment controls the open/close of the radiofrequency switch 16 as described above, the synchrotron 3 radiates an ion beam in a region (irradiation period Tb) where the vanes 331 are relatively thin at and near the vane bases 332 in the circumferential direction of the RMW 33, and does not radiate the ion beam in the other rotation angle region. In this case, a Bragg peak is formed at a position that is deep from the patient's body surface, and an SOBP is obtained accordingly at a position that is deep from the patient's body surface. In a situation where a beam is constantly extracted from the synchrotron 3 within a 360° rotation region in the circumferential direction of the RMW 33, it is possible to obtain a great SOBP width that ranges from the proximity of the patient's body surface to a deep position. When the operations for starting and terminating the ion beam radiation are controlled as described above in accordance with the rotation angle of the RMW 33, a plurality of SOBP widths can be formed with a single RMW 33.

A control process that is performed to adjust the intensity of the ion beam extracted from the synchrotron 3 during a period during which the ion beam is extracted within an operation cycle of the synchrotron 3, that is, the extraction control period (FIG. 2A), will now be described.

The timing system 50 outputs the extraction control start signal 501 to the extraction control signal processor 18. The extraction control start signal 501 is transmitted to the control processor 180. The control processor 180 outputs the extraction control start signal 501 to the control signal output unit 181b. Upon receipt of the extraction control start signal 501, the control signal output unit 181b exercises update control over the global intensity modulation signal 141 at fixed intervals in accordance with the global intensity modulation signal pattern data 403 stored in the storage device. In other words, update control is exercised over the global intensity modulation signal 141 at fixed intervals during the extraction control period.

The control signal output unit 181b also inputs a beam extraction control signal 160 from the control signal output unit 181c. If an ON signal for permitting the ion beam radiation is input as a beam extraction control signal 160 after the extraction control start signal 501 is input, the control signal output unit 181b exercises update control over the global intensity modulation signal pattern data 403 at the next address and outputs the global intensity modulation signal 141. If, on the other hand, an OFF signal for terminating the ion beam radiation is input as a beam extraction control signal 160, the control signal output unit 181b does not update the data and retains the last read output value of the global intensity modulation signal 141. As described above, when an ON signal for permitting the ion beam radiation is input as a beam extraction control signal 160, the control signal output unit 181b exercises update control over the global intensity modulation signal 40. When, on the other hand, an OFF signal for terminating the ion beam radiation is input as a beam extraction control signal 160, the control signal output unit 181b repeatedly retains the output value of the last output global intensity modulation signal 141 (the global intensity modulation signal 141 based on the last updated global intensity modulation signal pattern data). In other words, the control signal output unit 181b outputs the global intensity modulation signal 141 in consideration of beam intensity attenuation of the ion beam in the synchrotron 3 during a period (irradiation period Tb) during which the ion beam is extracted from the synchrotron 3 in accordance with the rotation angle of the RMW 33. During a period during which the synchrotron 3 does not extract the ion beam, the control signal output unit 181b outputs a global intensity modulation signal 141 that is based on the last updated global intensity modulation signal pattern data. As a result, the control signal output unit 181b outputs to the global intensity modulator 14 a global intensity modulation signal 141 that looks like FIG. 5-(c).

In the present embodiment, the extraction control signal processor 18 includes the multiplier circuit 182, which receives the layer A signal 341 and layer B signal 342 from the rotary encoder 34, multiplies them by four, and outputs the multiplied signals as the update clock signals 184. The use of the multiplier circuit 182 makes it possible to multiply the resolution of the update clock signals 184 by four and control the ion beam extraction due to RMW rotation with increased resolution. However, if the angle control resolution required for the RMW 33 is not high, an alternative would be to refrain from adding the multiplier circuit 182, use either the layer A output signal 341 or the layer B output signal 342 as an update clock signal 184, output the update clock signal 184 to the control signal output unit 181*b* or control signal output unit 181*c*, and handle the update clock signal 184 as an update signal for the local modulation signal pattern data 404 and beam extraction control pattern data 405.

When the target energy for the ion beam accelerated by the synchrotron 3 is to be changed, the accelerator control system 40 may output a setting update signal to the control processor 180 and allow the control processor 180 to control the extraction radiofrequency signal processor 20 in accordance with the setting update signal. This causes the extraction radiofrequency signal processor 20 to output an extraction radiofrequency signal 131 according to the changed target energy.

The relationship of the extracted beam intensity to the intensity of the radiofrequency signal applied to the circular beam is determined to define the first beam intensity modulation means for controlling the beam intensity of an ion beam extraction from the synchrotron 3 during an extraction control period within an operation cycle of the synchrotron 3. Amplitude control data providing constant extracted beam intensity is prepared from the determined relationship as pattern data, and used as a radiofrequency signal modulation signal for the amplitude control means, which is to be applied to the extraction radiofrequency application apparatus. Further, this modulation signal is updated only when the synchrotron 3 exercises extraction control over the ion beam. In this manner, beam intensity control can be provided over the extraction control period within an operation cycle of the synchrotron 3.

When an RMW irradiation method is used, means for controlling the beam intensity in accordance with the rotation angle of the RMW is provided as the second beam intensity modulation means for exercising control over a plurality of minute irradiation periods contained in the extraction control period within an operation cycle of the synchrotron 3. More specifically, means for detecting the rotation angle of the RMW, a gate signal representing the result of RMW rotation angle detection, an amplitude control pattern data signal representing the RMW rotation angle, means for exercising update control over the gate signal and amplitude control pattern data signal in accordance with changes in the RMW rotation angle, and amplitude modulation means for controlling the amplitude of the radiofrequency signal to be applied to the extraction radiofrequency application apparatus in accordance with the amplitude control pattern data signal updated according to the changes in the RMW rotation angle are prepared to control the amplitude of the radiofrequency signal to be applied to the extraction radiofrequency application apparatus in accordance with the result of RMW rotation angle detection.

It is preferred that a radiofrequency switch for controlling the radiofrequency signal output to the extraction radiofrequency application apparatus by using the gate signal that is output in accordance with the changes in the RMW rotation angle be prepared to provide the capability of rapidly cutting off the beam.

It is preferred that means for monitoring the intensity of the beam extracted from the synchrotron 3 and a function for exercising feedback control over the extracted beam intensity in accordance with the displacement between monitored extracted beam intensity and target extracted beam intensity be incorporated to provide the capability of inhibiting a beam intensity change upon each radiation.

The present embodiment provides the following advantages:

(1) The present embodiment can provide increased radiation safety because it enables the functions for exercising output control over the global intensity modulation signal 141 and local modulation signal 151 and controlling the radiofrequency switches 16, 17 during only the extraction control period of an operation cycle of the synchrotron.

(2) The present embodiment is configured so that the beam extraction control signal 160 enters the control signal output unit 181*b* and that update control is exercised over the global intensity modulation signal 141 in accordance with the beam extraction control signal 160. This ensures that update control is exercised only during the irradiation period (Tb) for the RMW 33, which is within the irradiation control period for ion beam extraction from the synchrotron 3. Therefore, enhanced control accuracy is provided for the beam intensity of an ion beam that moves in a circular path within the synchrotron 3.

(3) The present embodiment provides open/close control over the radiofrequency switch 17 in accordance with the beam extraction permission signal 602 from the safety interlock system 60 and provides open/close control over the radiofrequency switch 16 in accordance with the beam extraction permission signal 602 from the safety interlock system 60 and the beam extraction control signal 160 from the control signal output unit 181. Since the two radiofrequency switches 16, 17 are controlled in the manner described above, it is possible to avoid inadvertent radiation to the patient.

(4) The radiofrequency switch 16 is open/close controlled in accordance with a radiofrequency switch control signal 161 from the AND circuit 183, which is derived from the beam extraction control signal 160 and beam extraction permission signal 602. This ensures that ion beam extraction/extraction stop control is properly exercised in accordance with the rotation angle of the RMW 33 during the extraction control period. Further, the extraction radiofrequency signal processor 20 outputs the extraction radiofrequency signal 133 during the extraction control period only.

(5) The present embodiment can simultaneously control the global intensity modulation signal 141, beam extraction control signal 160, and local modulation signal 151 during the irradiation period (Tb) during which an ion beam is extracted from the synchrotron 3. Consequently, the present embodiment can form a desired extracted beam waveform 4*c*.

Second Embodiment

A particle beam therapy system according to a second embodiment of the present invention will now be described. The particle beam therapy system according to the present embodiment is configured so that the irradiation apparatus 32 of the particle beam therapy system 1 according to the first embodiment is replaced with an irradiation apparatus 32A for use with a scanning irradiation method. The irradiation apparatus 32A is obtained by removing the RMW 33 and rotation detector 34 from and adding a scanning magnet (not shown) to the irradiation apparatus 32. An extraction control apparatus 11A according to the present embodiment is obtained by removing the multiplier circuit 182 and AND circuit 183 from and adding a control logic device 185*a* to the extraction control apparatus 11 according to the first embodiment. The control logic device 185*a* is connected to the control processor for extraction 180 and the radiofrequency switch 16.

The scanning irradiation method according to the present embodiment is called a spot scanning irradiation method. The spot scanning irradiation method will now be summarized.

The spot scanning irradiation method exercises control so as to use a thin beam for irradiation, adjusts the magnetic field strength of the scanning magnet (not shown) to determine the irradiation position, and provides irradiation while managing the dose in the unit of a small radiation site called a spot. When the amount of radiation administered to a spot reaches a predetermined dose, the spot scanning irradiation method stops the beam radiation and repeatedly changes the irradiation position and irradiation beam energy before providing beam radiation.

Unlike the RMW irradiation method, which is shown in FIG. 7, the spot scanning irradiation method uses the control logic device 185a to provide control as described above. For the radiofrequency switch control signal 161 to be input into the radiofrequency switch 16 and the local modulation signal 151 to be input into the local intensity modulator 15, the control logic device 185a outputs the radiofrequency switch control signal 161 and a local modulation data update signal 185 when an AND condition for a period between the instant at which the irradiation start signal 35 is output from an irradiation control apparatus (not shown) and the instant at which a dose-attained signal 36 is output to indicate that a predetermined dose is reached by the amount of radiation administered to a radiation site is established during a period during which the beam extraction permission signal 602 is output within a synchrotron operation cycle. The control logic device 185a provides beam radiation at an irradiation time that is specified by the irradiation control apparatus.

An irradiation control method that is used with the spot scanning irradiation method will now be described in detail. First of all, the irradiation control apparatus confirms that magnetic field strength is completely set for the scanning magnet, and then outputs the irradiation start signal 35. Next, the irradiation control apparatus integrates a dose measurement signal from the dose monitor (not shown) included in the irradiation apparatus 32. When a predetermined dose is reached, the irradiation control apparatus outputs the dose-attained signal 36. Upon receipt of the dose-attained signal 36, the control logic device 185a outputs a control signal 161 to the radiofrequency switch 16 to open the radiofrequency switch 16. When the radiofrequency switch 16 opens, the output of the extraction radiofrequency signal 133 to the radiofrequency electrode 10 stops, thereby bringing the beam radiation to a stop.

After the beam radiation is stopped, the irradiation control apparatus changes the magnetic field strength of the scanning magnet. After the magnetic field strength change is confirmed, the irradiation control apparatus outputs the irradiation start signal 35. Upon receipt of the irradiation start signal 35, the control logic device 185a closes the radiofrequency switch 16 so that the extraction radiofrequency signal is applied to the radiofrequency electrode 10 to resume a beam radiation process. When the above beam radiation process is repeated to complete the radiation to the irradiation surface, which is called a layer, at a certain irradiation depth associated with the irradiation beam energy, the irradiation control apparatus outputs an energy update signal 37 to change the energy to be supplied from the accelerator.

When beam extraction control is exercised in the synchrotron 3, the center frequency of the radiofrequency signal to be applied to the extraction radiofrequency electrode 10 varies with energy. Therefore, a plurality of frequency data that are to be set for the extraction radiofrequency oscillator 12 should be prepared in a memory 181a in accordance with the energy for radiation.

Figure 9:
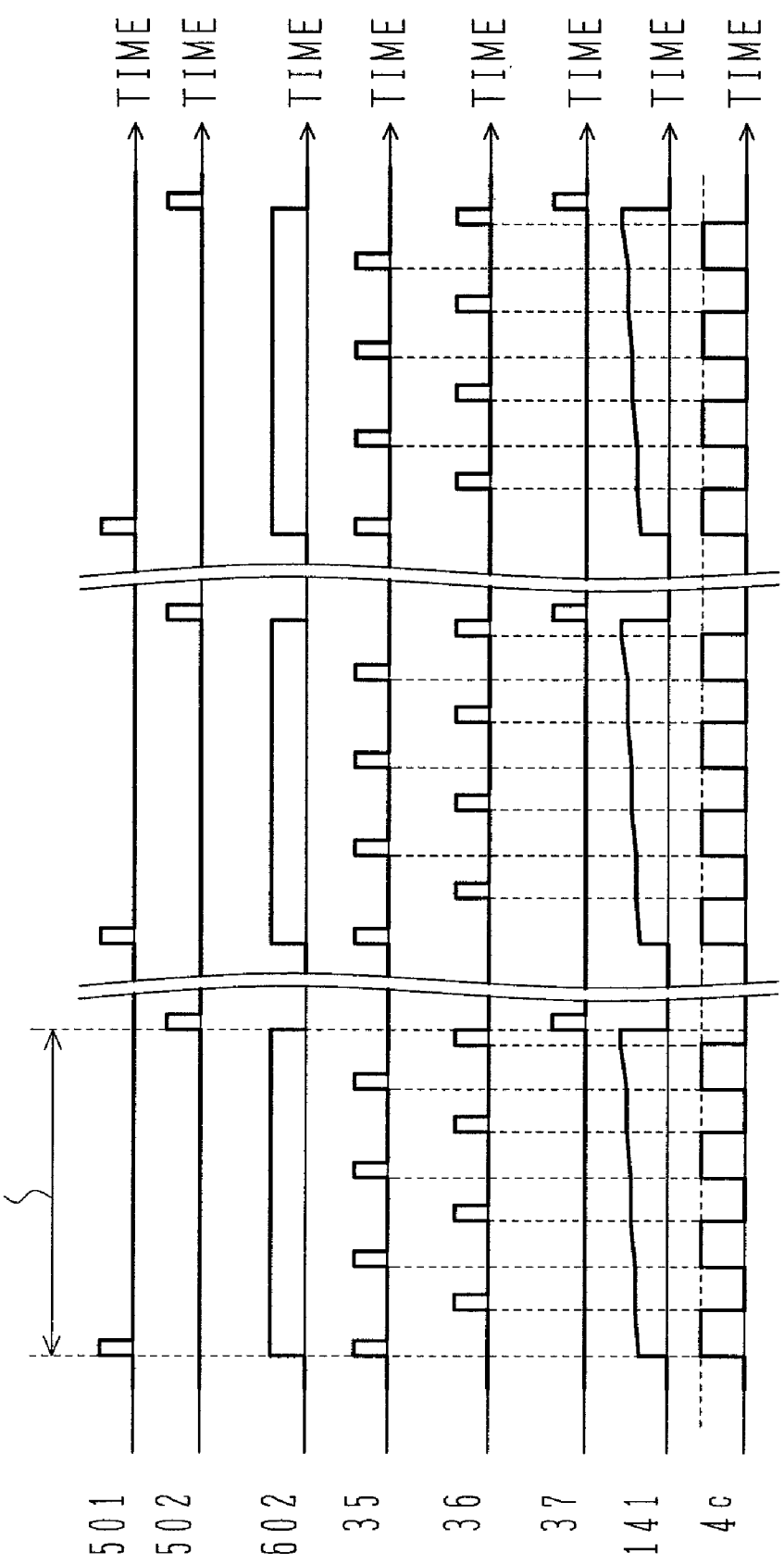
FIG. 9 is a timing diagram illustrating a radiation control period of an operation cycle of the synchrotron that is operated according to the scanning irradiation method.

As is obvious from a timing diagram in FIG. 9, the scanning irradiation method does not require rotation-control-based pattern data control unlike the RMW irradiation method. However, the scanning irradiation method requires the use of the control logic device 185a, which outputs the irradiation start signal 35 and dose-attained signal 36 for each spot, the energy update signal 37, the radiofrequency switch control signal 161, and the local modulation data update signal 185.

For energy change control, the spot position is predetermined for each irradiation depth. Therefore, when a radiation process is completed for all the spots within an irradiation area, the irradiation control apparatus outputs the energy update signal 37 to the accelerator control system 40. The accelerator control system 40 outputs an energy update signal 37 to the extraction control apparatus 18 in accordance with the energy update signal 37 from the irradiation control apparatus. This energy update signal 37 updates the frequency data 121 that are to be set for the extraction radiofrequency oscillator 12. As is the case with the RMW irradiation method, the scanning irradiation method uses the global intensity modulator 14 and local intensity modulator 15 in order to maintain a constant beam intensity during extraction control.

The global intensity modulation signal 141 to be set for the global intensity modulator 14 is updated in accordance with the pattern data update signal 185 for beam extraction control only during beam radiation control. While the beam radiation is stopped, however, control is exercised so that the global intensity modulation signal 141 remains unchanged. As far as a fixed value is constantly set for the local modulation signal 151, control is exercised so that a constant beam intensity prevails during the extraction control period of an operation cycle of the synchrotron.

When the scanning irradiation method is used, a beam radiation signal that is controlled in accordance with the beam radiation dose for a diseased part radiation spot, an amplitude control data signal for a radiofrequency signal that permits the radiation of a fixed-intensity beam to the diseased part, and amplitude control means for controlling the radiofrequency signal intensity in accordance with the amplitude control data signal are provided to control the radiofrequency signal to be applied to the extraction radiofrequency electrode in accordance with the beam radiation signal. As is the case with the RMW irradiation method, the scanning irradiation method can rapidly cut off the beam by using a radiofrequency switch that controls the radiofrequency signal output to the extraction radiofrequency electrode in accordance with the beam radiation signal.

The present embodiment provides the same advantages as the first embodiment.

Third Embodiment

Figure 5:
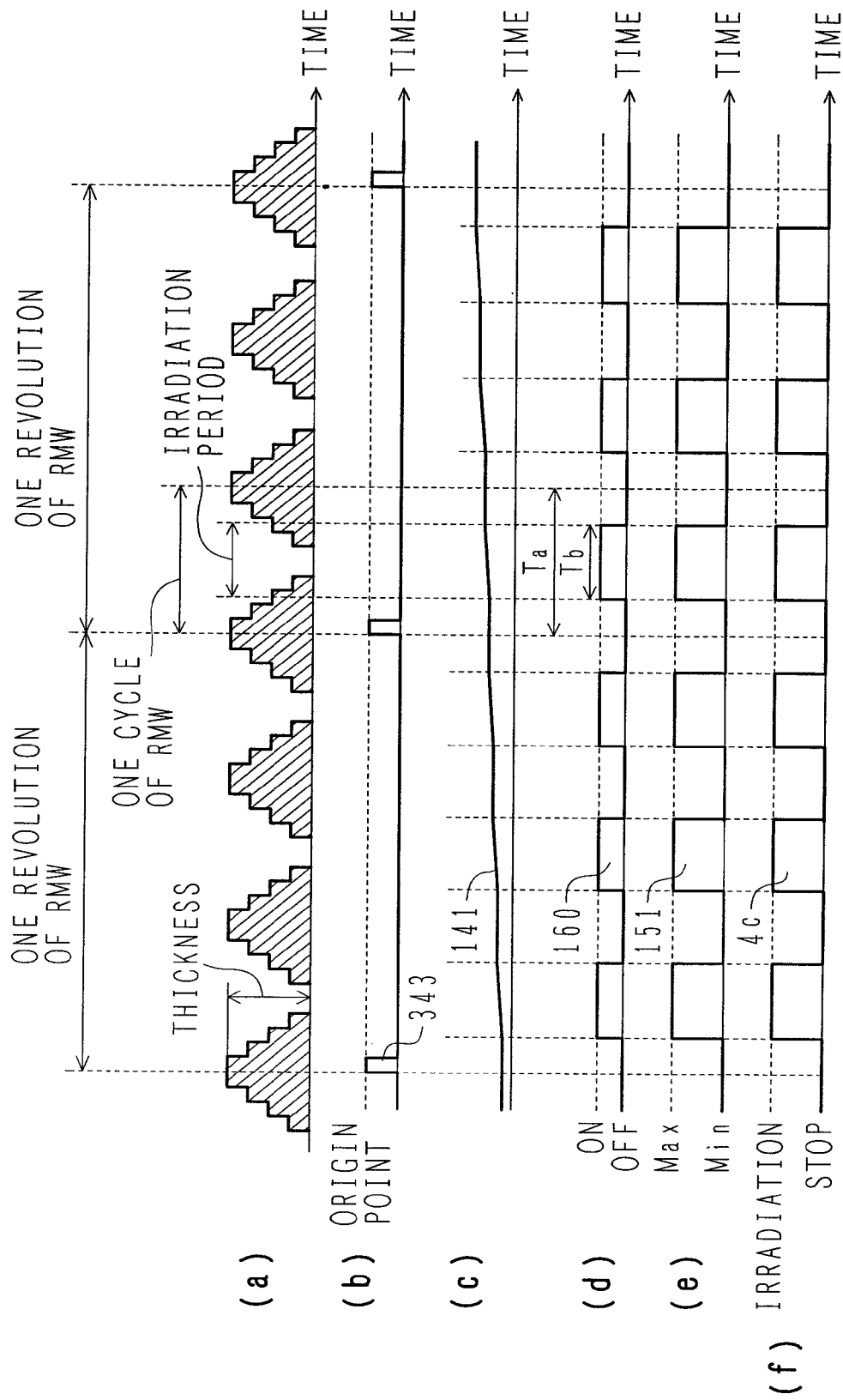
FIG. 5 is a timing diagram illustrating one cycle of the RMW that is operated according to the RMW irradiation method.
Figure 10:
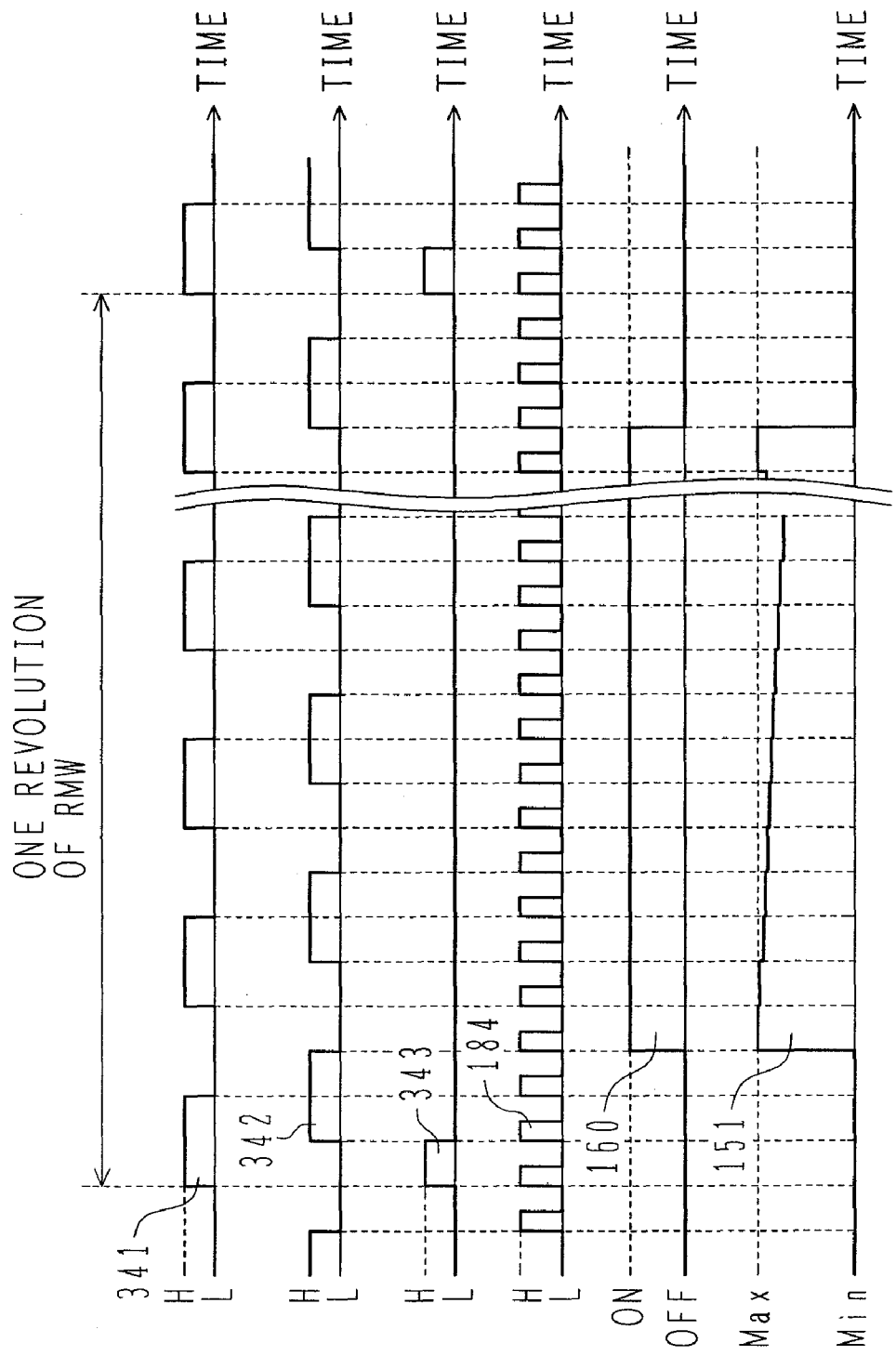
FIG. 10 is a typical timing diagram illustrating one revolution of the RMW that is operated according to the RMW irradiation method.

A particle beam therapy system according to a third embodiment of the present invention will now be described. The particle beam therapy system according to the present embodiment is configured similar to the particle beam therapy system according to the first embodiment. As shown in FIG. 5-(e), the control signal output unit 181c according to the first embodiment outputs the local modulation signal 151 that does not vary with time during the irradiation period (Tb). However, the control signal output unit 181c according to the present embodiment outputs the local modulation signal 151 that varies with time during the irradiation period (Tb), as shown in FIG. 10. The local modulation signal 151 controls the intensity of the ion beam extracted from the synchrotron 3 in accordance with the rotation angle of the RMW 33. When the local modulation signal 151 is varied in accordance with the rotation angle of the RMW 33 as described in conjunction with the present embodiment, the intensity of the ion beam extracted from the synchrotron 3 can be varied in accordance with the rotation angle of the RMW 33. When local modulation control is exercised in the above manner, the RMW 33 can form an SOBP having an arbitrary shape.

Fourth Embodiment

Figure 11:
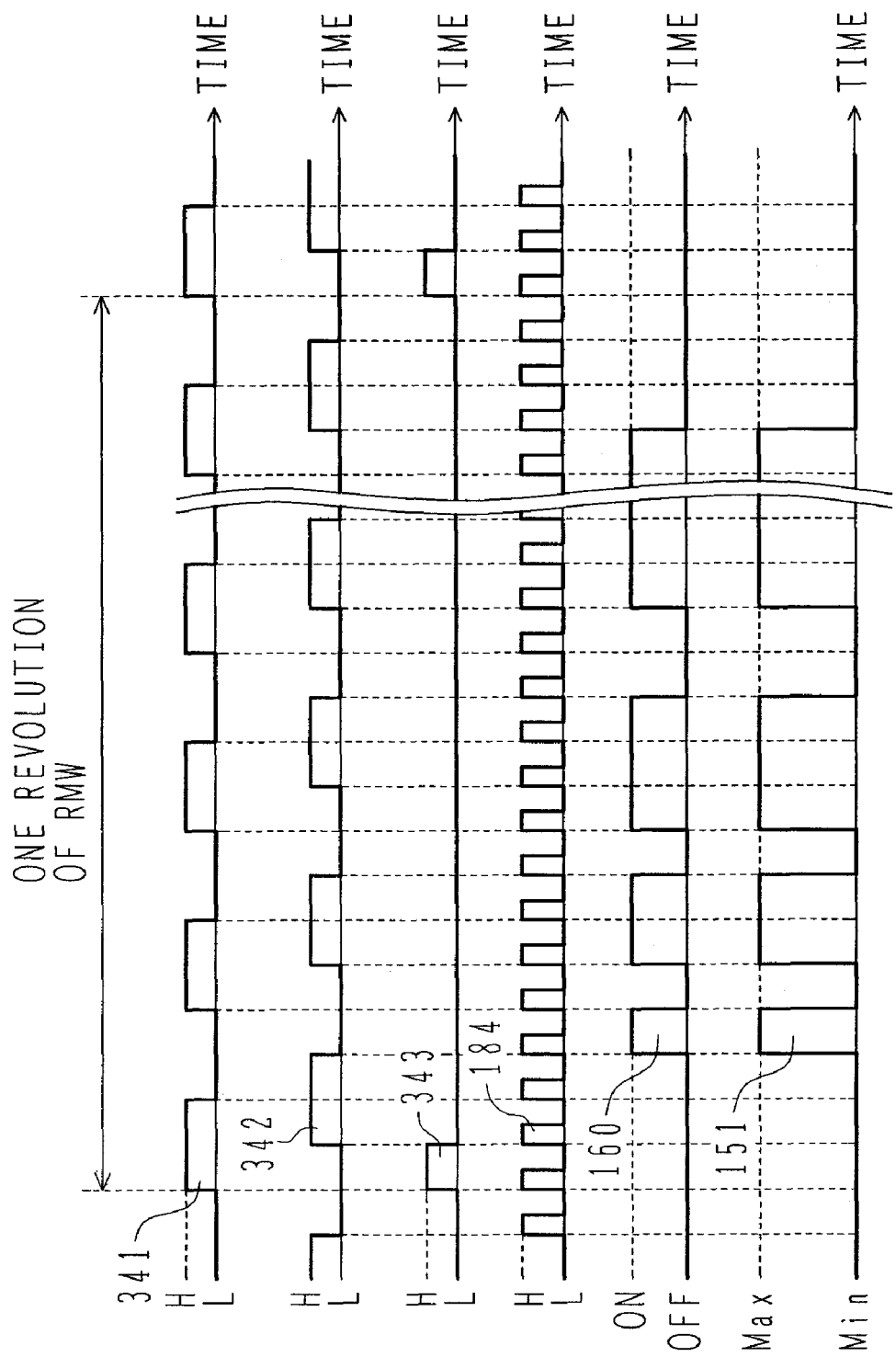
FIG. 11 is another typical timing diagram illustrating one revolution of the RMW that is operated according to the RMW irradiation method.

A particle beam therapy system according to a fourth embodiment of the present invention will now be described. The particle beam therapy system according to the present embodiment is configured similar to the particle beam therapy system according to the third embodiment (see FIG. 7). The present embodiment differs from the third embodiment in that the data structures of the local modulation signal 151 and beam extraction control signal 160 vary intermittently (see FIG. 11). When modulation control is implemented as described above, it is possible to expressly manage the extraction control time for beam extraction control. Further, when pulse control is repeatedly exercised as described above, it is possible to provide PWM (Pulse Width Modulation) control, which differs from AM modulation control based on a fixed value as shown in FIG. 6. When the pulse structure of the local modulation signal 151 is properly controlled, it is possible to offer a new SOBP formation method for use with the RMW irradiation method. To implement beam intensity PWM control as described above, it is necessary to exercise constant amplitude control during a charged particle beam irradiation period. As such being the case, the present embodiment can radiate a beam having a fixed intensity over the irradiation period by exercising update control over the global intensity modulation signal 141, which is to be set for the global intensity modulator 14, only at the time of beam radiation.

Fifth Embodiment

Figure 12:
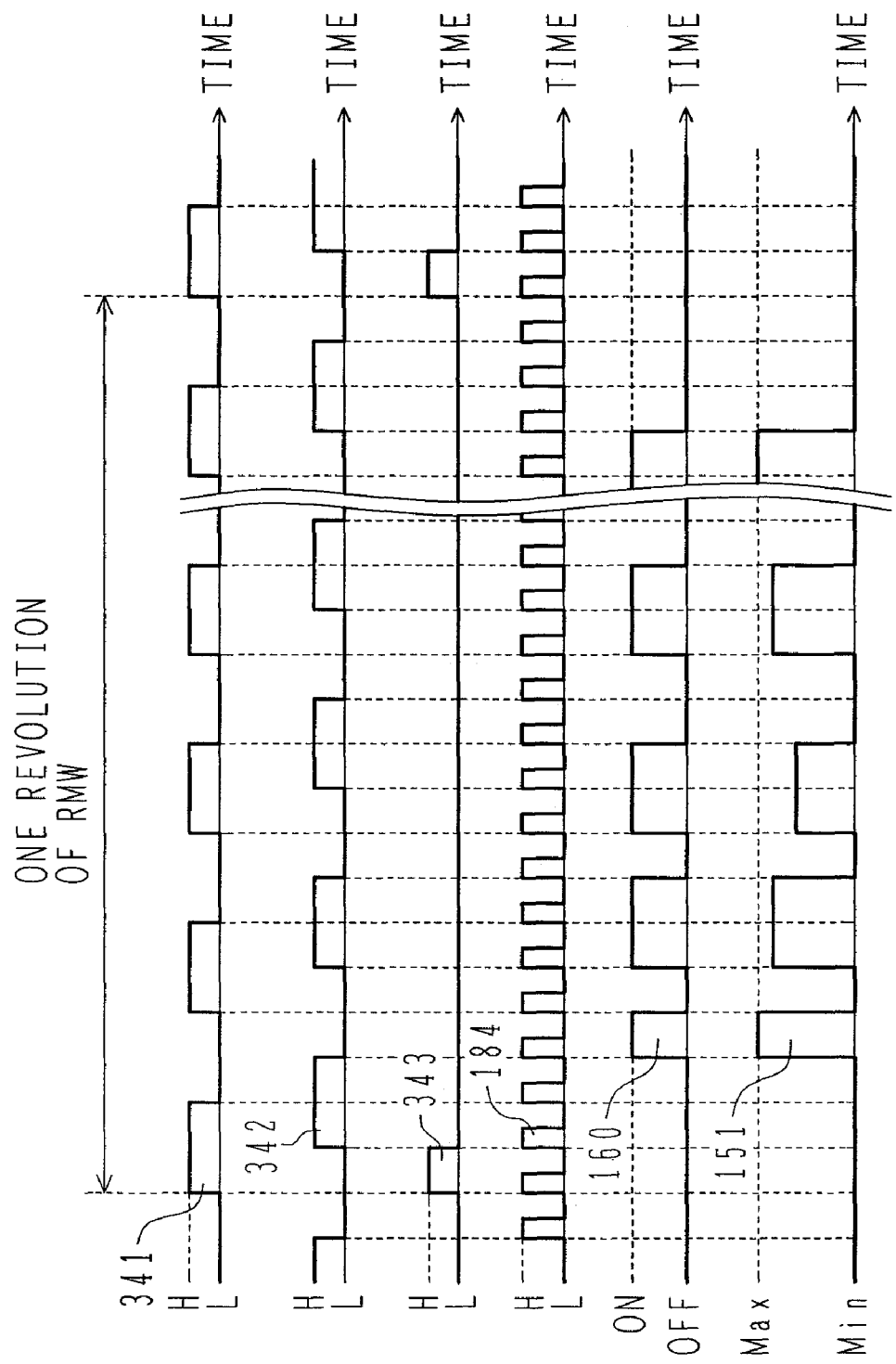
FIG. 12 is still another typical timing diagram illustrating one revolution of the RMW that is operated according to the RMW irradiation method.

A particle beam therapy system according to a fifth embodiment of the present invention will now be described. The particle beam therapy system according to the present embodiment is configured similar to the particle beam therapy system according to the fourth embodiment (see FIG. 7). The present embodiment differs from the fourth embodiment in that the data structures of the local modulation signal 151 and beam extraction control signal 160 vary intermittently and that the amplitude of the local modulation signal 151 varies with output setup time (see FIG. 12). This makes it possible to vary the intensity at a certain angle of the RMW and offer a new SOBP formation method for use with the RMW irradiation method. In this instance, the present embodiment can radiate a beam having a desired intensity over the irradiation period by exercising update control over the global intensity modulation signal 141, which is to be set for the global intensity modulator 14, only at the time of beam radiation.

Sixth Embodiment

Figure 8:
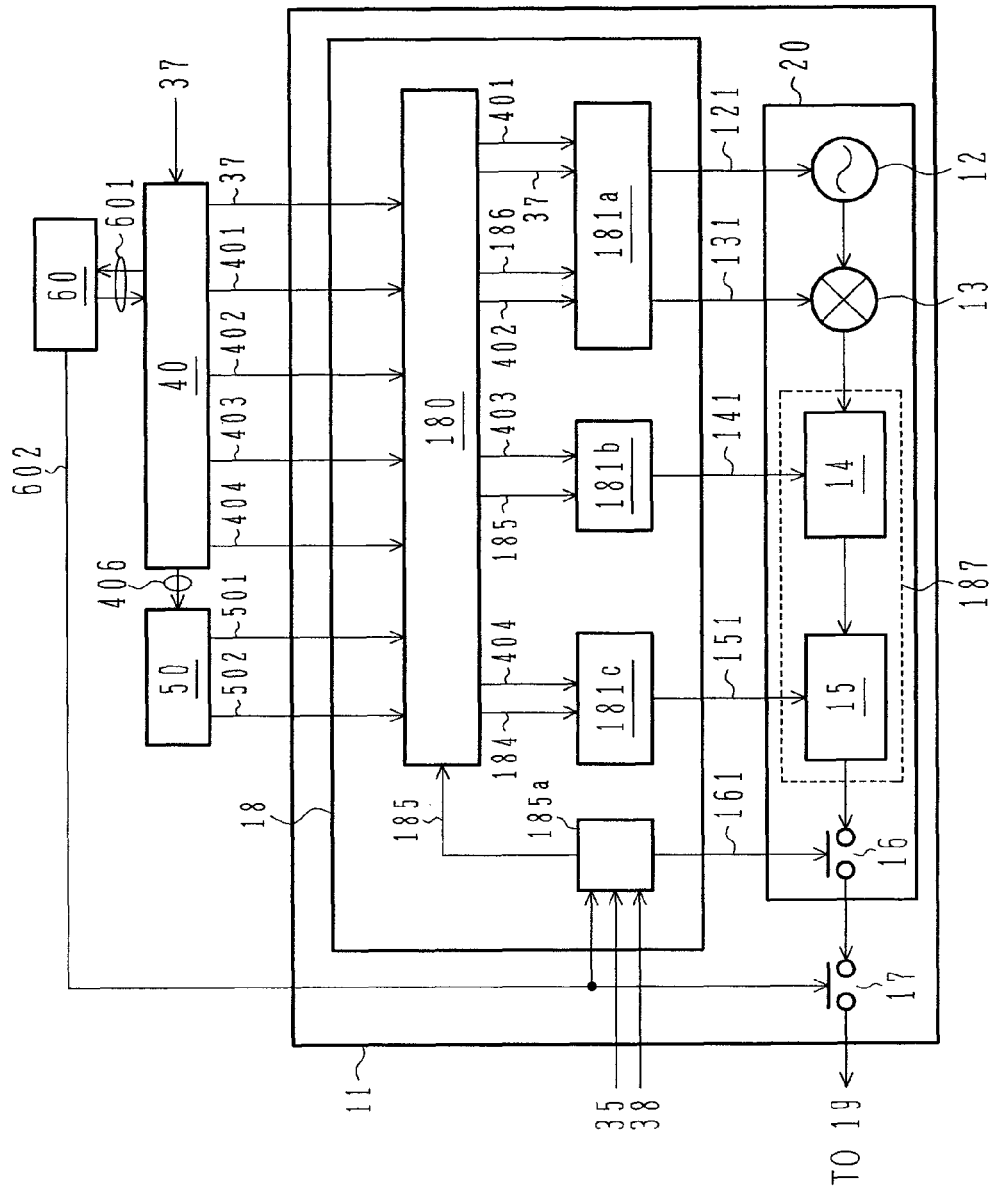
FIG. 8 shows the configuration of an extraction control apparatus that is operated according to a scanning irradiation method.
Figure 13:
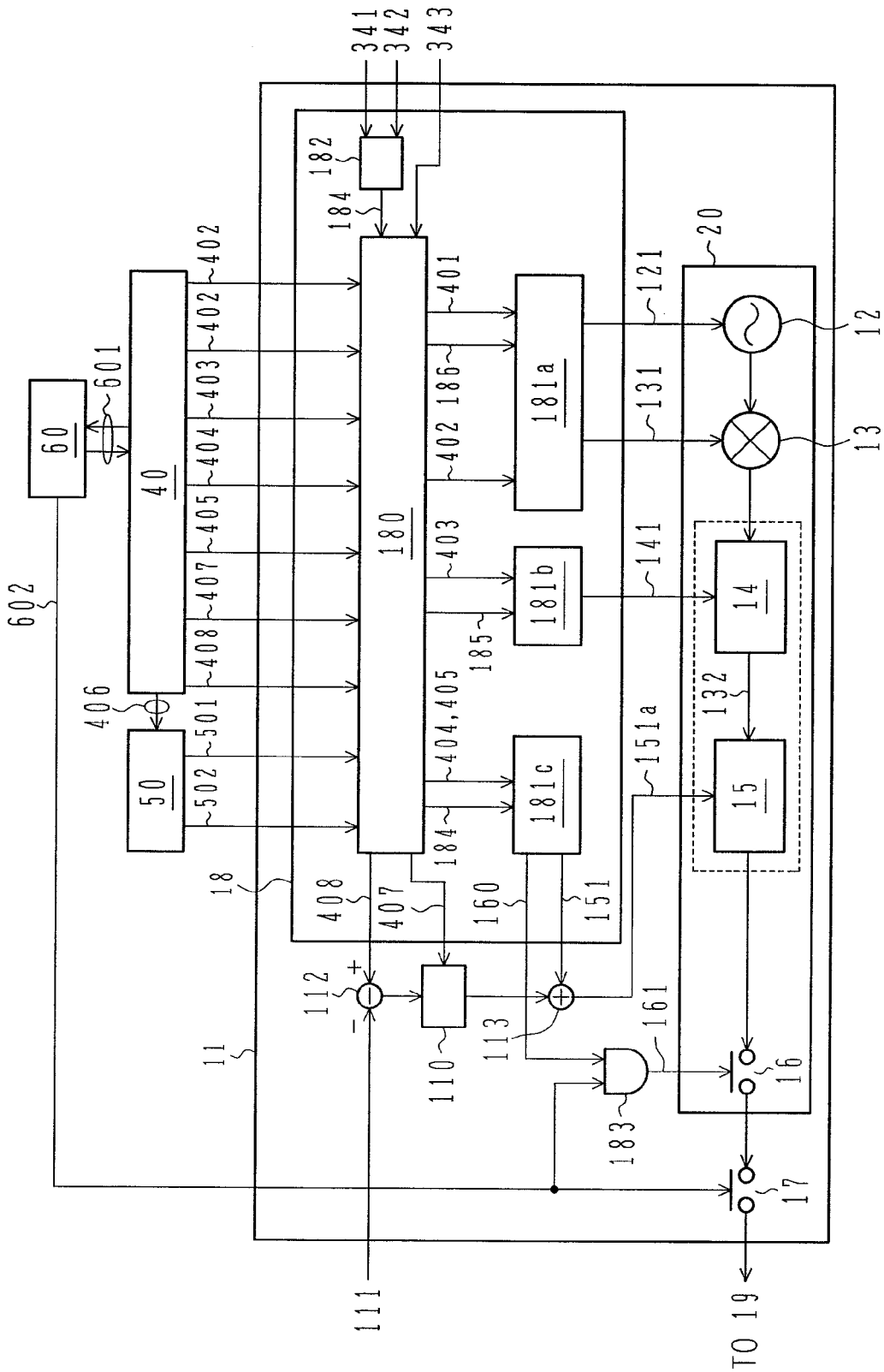
FIG. 13 shows the configuration of an extraction control apparatus that provides beam intensity feedback control according to the RMW irradiation method.

A particle beam therapy system according to a sixth embodiment of the present invention will now be described. The particle beam therapy system according to the present embodiment is configured similar to the particle beam therapy system according to the first embodiment (see FIG. 7). The present embodiment differs from the first embodiment in that a feedback arithmetic processing circuit is incorporated (see FIG. 13). The feedback arithmetic processing circuit includes a difference circuit 112 that computes an extracted beam intensity observed value 111, an extracted beam intensity target value 408, and the difference between the observed value and target value; a compensation control circuit 110 that is based on the result output from the difference circuit 112; and an addition computation circuit 113 that handles a gain setting 407 for the compensation control circuit 110, an output value generated from the compensation control circuit 110, and the local modulation signal 151. This makes it possible to exercise feedback control over the extracted beam intensity during the use of the RMW irradiation method. The present embodiment uses a fixed value as the extracted beam intensity target value 408. For better results, however, the target value 408 should be stored in a memory 181c as pattern data and updated by the pattern data update signal 184 according to the rotation angle of the RMW. Further, when the same feedback arithmetic processing circuit as above is used with the scanning irradiation method shown in FIG. 8, it is possible to exercise feedback control over the beam intensity during scanning irradiation control as well.

What is claimed is:

1. A particle beam irradiation system comprising:
   a synchrotron for accelerating and extracting a charged particle beam;
   an irradiation apparatus for radiating the charged particle beam extracted from said synchrotron; and
   an extraction control apparatus for controlling extraction of the charged particle beam from said synchrotron:
   said extraction control apparatus including:
   first beam intensity modulation means for controlling the beam intensity of the charged particle beam extracted from said synchrotron during an extraction control period of an operation cycle of said synchrotron; and
   second beam intensity modulation means for controlling the beam intensity of the charged particle beam extracted from said synchrotron during each of a plurality of irradiation periods contained in the extraction control period of the operation cycle.

2. The particle beam irradiation system according to claim 1, wherein said irradiation apparatus has a rotatable energy modulator whose axial direction thickness varies with the direction of rotation, and wherein said second beam intensity modulation means controls the beam intensity of the charged particle beam extracted from said synchrotron in accordance with the rotation angle of the energy modulator.

3. The particle beam irradiation system according to claim 2, further comprising:
   an angle detector for detecting the rotation angle of the energy modulator;
   origin point detection means for detecting the origin points of the energy modulator; and
   a storage device for storing the beam intensity of the charged particle beam extracted from said synchrotron, which corresponds to the axial direction thickness relative to the angles from a plurality of origin points of the energy modulator,
   wherein said second beam intensity modulation means selects the beam intensity from the storage device in accordance with the rotation angle from the angle detector relative to a detection signal from the origin point detection means, and controls the beam intensity of the charged particle beam extracted from said synchrotron in accordance with the selected beam intensity.

4. The particle beam irradiation system according to claim 1, wherein said irradiation apparatus has a rotatable energy modulator whose axial direction thickness varies with the direction of rotation, and wherein said second beam intensity modulation means provides control to vary the beam intensity of the charged particle beam extracted from said synchrotron in accordance with the thickness of the energy modulator while the charged particle beam is radiated.

5. A particle beam irradiation system comprising:
   a synchrotron for accelerating and extracting a charged particle beam;
   an irradiation apparatus for radiating the charged particle beam extracted from said synchrotron; and
   an extraction control apparatus for controlling extraction of the charged particle beam from said synchrotron:
   said extraction control apparatus including:
   a first beam intensity modulator which controls the beam intensity of the charged particle beam extracted from said synchrotron during an extraction control period of an operation cycle of said synchrotron; and
   a second beam intensity modulator which controls the beam intensity of the charged particle beam extracted from said synchrotron during each of a plurality of irradiation periods contained in the extraction control period of the operation cycle.

6. The particle beam irradiation system according to claim 5, wherein said irradiation apparatus has a rotatable energy modulator whose axial direction thickness varies with the direction of rotation, and wherein said second beam intensity modulator controls the beam intensity of the charged particle beam extracted from said synchrotron in accordance with the rotation angle of the energy modulator.

7. The particle beam irradiation system according to claim 6, further comprising:
   an angle detector which detects the rotation angle of the energy modulator;
   origin point detector which detects the origin points of the energy modulator; and
   a storage device for storing the beam intensity of the charged particle beam extracted from said synchrotron, which corresponds to the axial direction thickness relative to the angles from a plurality of origin points of the energy modulator,
   wherein said second beam intensity modulator selects the beam intensity from the storage device in accordance with the rotation angle from the angle detector relative to a detection signal from the origin point detector, and controls the beam intensity of the charged particle beam extracted from said synchrotron in accordance with the selected beam intensity.

8. The particle beam irradiation system according to claim 5, wherein said irradiation apparatus has a rotatable energy modulator whose axial direction thickness varies with the direction of rotation, and wherein said second beam intensity modulator provides control to vary the beam intensity in accordance with the thickness of the energy modulator while the charged particle beam is radiated.

* * * * *